US011253650B2

(12) United States Patent
Carlsson et al.

(10) Patent No.: US 11,253,650 B2
(45) Date of Patent: Feb. 22, 2022

(54) ELECTRICAL INFORMATION DEVICE FOR COMMUNICATING INFORMATION RELATED TO A MEDICAMENT DELIVERY

(71) Applicant: CAREBAY EUROPE LTD, Sliema (MT)

(72) Inventors: Daniel Carlsson, Enskede (SE); Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 464 days.

(21) Appl. No.: 16/073,670

(22) PCT Filed: Dec. 15, 2016

(86) PCT No.: PCT/EP2016/081215
§ 371 (c)(1),
(2) Date: Jul. 27, 2018

(87) PCT Pub. No.: WO2017/129314
PCT Pub. Date: Aug. 3, 2017

(65) Prior Publication Data
US 2019/0001069 A1    Jan. 3, 2019

(30) Foreign Application Priority Data
Jan. 29, 2016 (EP) .................................... 16153312

(51) Int. Cl.
*A61M 5/178* (2006.01)
*A61M 5/20* (2006.01)
(Continued)

(52) U.S. Cl.
CPC ............ *A61M 5/20* (2013.01); *A61M 5/2033* (2013.01); *A61M 5/3157* (2013.01);
(Continued)

(58) Field of Classification Search
CPC .... A61M 5/20; A61M 5/2033; A61M 5/3157; A61M 5/31568; A61M 5/3158; A61M 2005/2013; G16H 20/17
See application file for complete search history.

(56) References Cited

U.S. PATENT DOCUMENTS 6,171,276 B1   1/2001  Lippe et al.
9,724,475 B2   8/2017  Krulevitch et al.
(Continued)

FOREIGN PATENT DOCUMENTS

CN    102413852 A   4/2012
CN    102413856 A   4/2012
(Continued)

OTHER PUBLICATIONS

Communication issued in European Patent Application No. 16812748.8 dated Nov. 5, 2019.
(Continued)

*Primary Examiner* — Rebecca E Eisenberg
*Assistant Examiner* — Tania Ismail
(74) *Attorney, Agent, or Firm* — McDonnell Boehnen Hulbert & Berghoff LLP

(57) ABSTRACT

An electrical information device and a medicament delivery device are presented. The electrical information device includes at least one start of delivery sensor configured to detect a distal axial movement of a release member of the medicament delivery device. The release member is configured to be distally moved when an activator member of the medicament delivery device 1 is forced distally. The electrical information device also includes at least one information communication unit, which is configured to communicate information related to the medicament delivery. The electrical information device further includes at least one activation unit, which is configured to activate the at least one information communication unit based on a detected distal axial movement of the release member.

20 Claims, 9 Drawing Sheets

(51) Int. Cl.
  *A61M 5/315*  (2006.01)
  *G16H 20/17*  (2018.01)
  *A61M 5/32*  (2006.01)

(52) U.S. Cl.
  CPC ...... *A61M 5/3158* (2013.01); *A61M 5/31568* (2013.01); *A61M 5/3204* (2013.01); *G16H 20/17* (2018.01); *A61M 2005/2013* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 2002/0133114 A1* | 9/2002 | Itoh | A61P 7/04 604/67 |
| 2014/0041658 A1* | 2/2014 | Goodman | A61M 15/06 128/203.14 |
| 2014/0074041 A1* | 3/2014 | Pedersen | A61M 5/31541 604/211 |

FOREIGN PATENT DOCUMENTS

| | | |
|---|---|---|
| CN | 103520806 A | 1/2014 |
| CN | 104334217 A | 2/2015 |
| CN | 104755118 A | 7/2015 |
| EP | 2190506 B1 | 8/2011 |
| EP | 2926846 A1 | 10/2015 |
| JP | 2012519026 A | 8/2012 |
| JP | 2012519028 A | 8/2012 |
| WO | 2010/098928 A1 | 9/2010 |
| WO | 2010/098931 A1 | 9/2010 |
| WO | 2012127046 A2 | 9/2012 |
| WO | 2014/154490 A2 | 10/2014 |

OTHER PUBLICATIONS

International Search Report and Written Opinion for Int. App. No. PCT/EP2016/081215, dated Mar. 28, 2017.

* cited by examiner

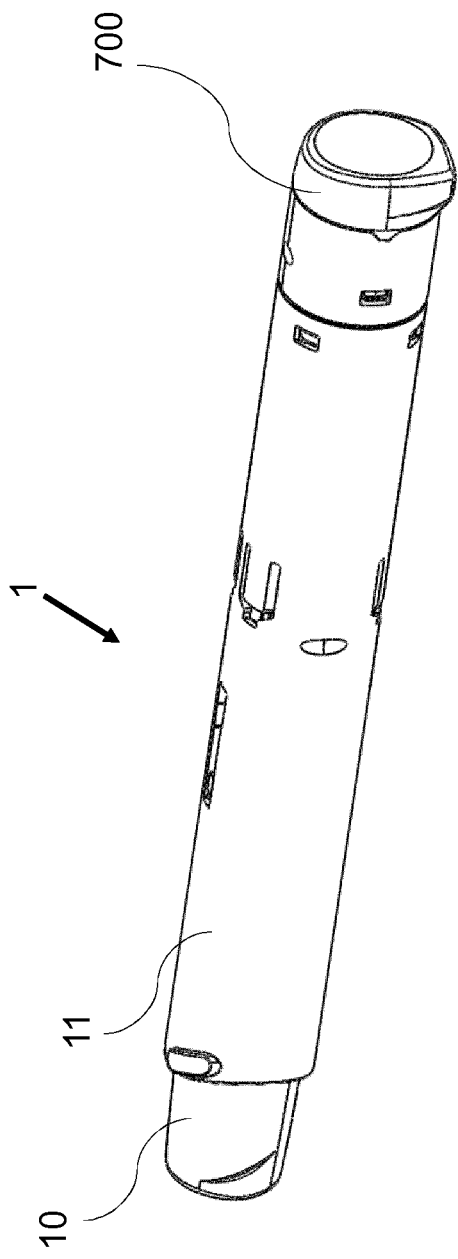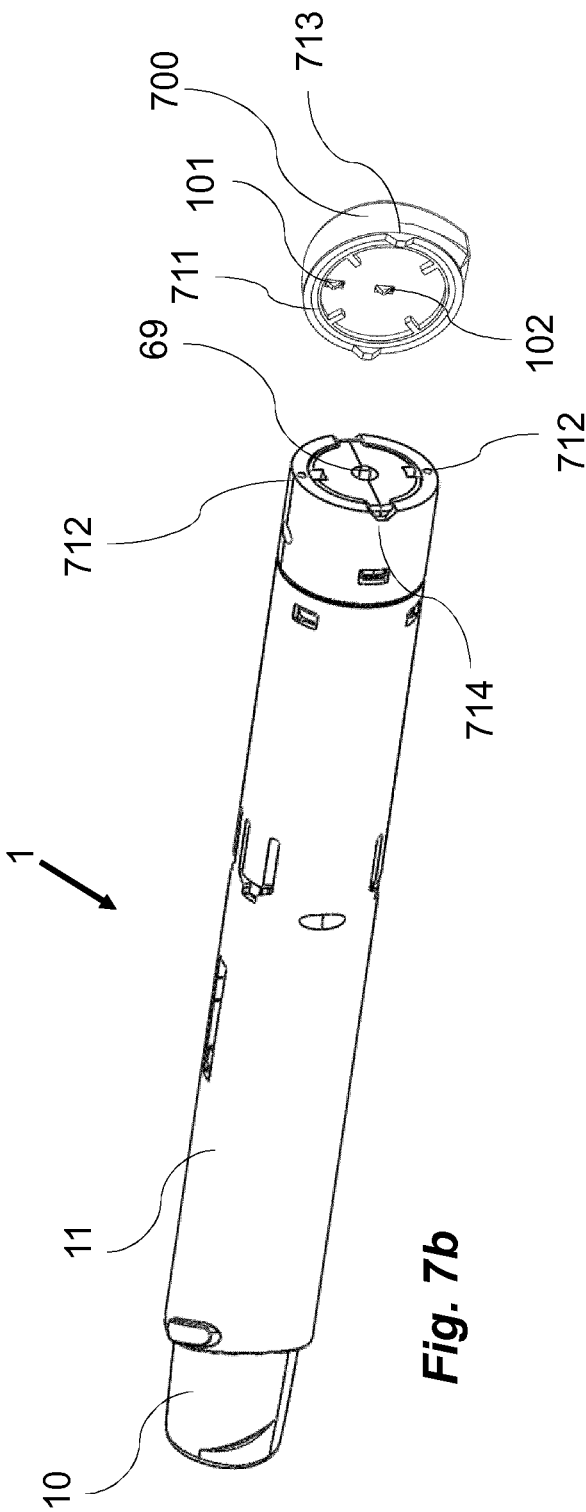
*Fig. 7a*
*Fig. 7b*

ELECTRICAL INFORMATION DEVICE FOR COMMUNICATING INFORMATION RELATED TO A MEDICAMENT DELIVERY

CROSS REFERENCE TO RELATED APPLICATIONS

The present application is a U.S. National Phase Application pursuant to 35 U.S.C. § 371 of International Application No. PCT/EP2016/081215 filed Dec. 15, 2016, which claims priority to European Patent Application No. 16153312.0 filed Jan. 29, 2016. The entire disclosure contents of these applications are herewith incorporated by reference into the present application.

FIELD OF INVENTION

The present invention relates to an electrical information device as defined in the preamble of claim 1, and to a medicament delivery device as defined in the preamble of claim 15.

BACKGROUND OF INVENTION

The following background information is a description of the background of the present invention, which thus not necessarily has to be a description of prior art.

Medicament delivery devices, such as for example injection devices, auto-injection devices or pen-injection devices, are nowadays commonly used for helping patients to take their medicaments/drugs. Such medicament delivery devices may have one or more automatic functions providing/facilitating the delivery of the medicaments, such as for example automatic penetration, automatic injection and/or automatic safety means for preventing from accidental needle sticks.

The medicament delivery devices can e.g. be activated by pressing the device against a dose delivery site, normally being a body part. The device can then be pressed against the body part for example by the patient and/or by trained personnel, such as physicians or nurses. The medicament delivery devices often comprise a housing, a spring acting on a plunger rod which in its turn acts on a stopper inside a medicament container for expelling the medicament through a needle attached to the container when being pressed against the body part. Hereby, an automatic or semiautomatic delivery of the medicament is provided by the device.

Medicament delivery devices help patients taking their medicaments. Especially, the right dosage of the medicament is secured by use of the device itself, since the amount of medicament/drug in the medicament container can be set/chosen to correspond to the prescribed dose. Normally, the medicament delivery device is essentially completely emptied by the delivery, whereby the prescribed dose of medicament is injected to the patient.

However, if the medicament delivery device is not held/pressed against the dose delivery site long enough, there is a risk that the medicament is not completely absorbed by the tissue of the patient. Preferably, the medicament delivery device should be held against the dose delivery site until the medicament container has been completely emptied and also during a predetermined time period after the medicament delivery has been ended. For patients having a need for taking medicaments, it has been proved to be difficult to know/understand when to remove the medicament delivery device from the dose delivery site. Many patients have therefore removed the medicament delivery device too soon, which results in that the actual dose of medicament being absorbed by the tissue of the patient is smaller than the prescribed dose. Thus, due to a patient uncertainty regarding how long the medicament delivery device should be held against the dose delivery site, the prescribed dose is often not provided to the patient.

On the other hand, some patient tend to hold the medicament delivery device far too long against the dose delivery site to be sure that the whole dose is taken. Hereby, the patient suffers from the inconvenience of medicament delivery during an unnecessarily long time.

Also, the adherence/compliance to take the medicaments according to a prescribed scheme over time is poor for some patients and/or patient groups. There can be many reasons for such non-compliance. One reason can be that the patient is in pain and/or that the delivery of the medicament itself is unpleasant, or maybe even painful. Another reason can be that the patient simply forgets to take the medicament. It should be noted that some sicknesses/diseases/conditions and/or medicaments affect the ability to remember things, and therefore increase the risk for the patient to forget taking the medication.

When the patient does not take the prescribed dose and/or does not follow the prescribed medication scheme, there is a risk that the sickness/disease/condition is prolonged or worsened, and/or that the patient is stricken with further complications. A prolonged or worsened sickness/disease/condition and/or further complications of course adds both to the suffering of the patient and to the total costs for the medicaments and medical care. Therefore, medical care personal treating the patient, as well as authorities and/or insurance companies paying for the treatment, want to be able to monitor the intake of medicaments for the patient.

Today, the intake of the medicaments can be estimated based on a count of how many of the prescriptions having been made up for a patient that are actually collected by the patient at e.g. a pharmacy. This is, however, a very uncertain method, since it is not at all guaranteed that collected medicaments are also taken by the patient.

The intake of medicaments can today also be monitored by the use of applications/computer programs, in which the patient himself/herself can enter data after each time a medicament dose has been taken. However, the probability that patients being likely not to take the medicament properly would remember and/or go through the extra work to enter data into such applications/computer programs is low. Thus, the information gathered by such applications/computer programs is very unreliable. Also, it is not at all certain that a missed entry in the application/computer program means that the medicament has not been taken. It is also not guaranteed that an entry in the application/computer program means that the medicine was taken.

SUMMARY OF INVENTION

It is therefore an object to solve at least some of the above mentioned disadvantages and to provide a device which helps taking the prescribed medicament dose and/or facilitates reliable monitoring of that patients follow their prescribed medication scheme, i.e. that the patients take the prescribed dose at the prescribed time instants.

The object is achieved by the above mentioned electrical information device according to the characterizing portion of claim 1.

According to an aspect of the present invention, an electrical information device arranged for communicating information related to a medicament delivery is presented. The electrical information device includes:

at least one start of delivery sensor configured to detect a distal axial movement of a release member of the medicament delivery device, the release member being configured to be distally moved when an activator member of the medicament delivery device is forced distally by the medicament delivery device being pressed against a dose delivery site;

at least one information communication unit configured to communicate the information; and at least one activation unit configured to activate the at least one information communication unit based on the detected distal axial movement of the release member.

By usage of the present invention, the suffering of the patients can be minimized. Also, the overall cost for medical care can be lowered for some patients and/or patient groups.

The present invention facilitates taking a prescribed dose of a medicament. The present invention also makes it possible for automated and reliable monitoring of whether patients follow their prescribed medication schemes or not. Based on this monitoring, e.g. a doctor treating a patient can directly contact a patient not following the medication scheme to hear what the problem is. Thus, the monitoring could help a doctor to find out which of his patients that need additional information and/or help with taking the medicaments. Maybe, the doctor could also come to the conclusion that a change of medicament should be made in order to increase the compliance of the patient, e.g. if the prescribed medicament is unpleasant/uncomfortable for the patient to take.

Also, authorities and/or insurance companies paying for the medical care can, based on the monitoring, contact the patient to inform the patient that they will stop paying for the treatment if the patient does not follow the prescribed medication scheme. An insurance company could also use the monitoring for adjusting the pricing level of a health care insurance for the patient.

The present invention can thus be used for improving the compliance to a prescribed medicament dose and/or to a medication scheme, which lowers the risk for a prolonged sickness/disease/condition and/or lowers the risk that the patient is stricken with further complications. Hereby, the suffering for the patient is minimized, and the total costs for the medicaments and medical care are also lowered.

According to an embodiment of the present invention, the electrical information device further includes at least one end of delivery sensor configured to detect a predetermined proximal axial movement of a plunger rod of the medicament delivery device, the predetermined proximal axial movement having a length $L_{pre}$ corresponding to a completed delivery of the medicament.

According to an embodiment of the present invention, an end of dose signaling member is configured to lose its support from the plunger rod when the plunger rod of the medicament delivery device has moved the length $L_{pre}$ proximally, whereby the end of dose signaling member is configured to be released from an initial fixed position and to perform an axial distal movement being detectable by the end of delivery sensor.

According to an embodiment of the present invention, the end of delivery sensor includes one or more in the group of:

at least one mechanical switch configured to be compressed by a distal movement of the end of dose signaling member;

at least one mechanical switch configured to be compressed by a distal movement of at least one guide rod member being arranged within the end of dose signaling member;

at least one electrical contact configured to be short-circuited by a distal movement of the end of dose signaling member; and at least one electrical contact configured to be short-circuited by a distal movement of at least one guide rod member being arranged within the end of dose signaling member.

According to an embodiment of the present invention, the at least one start of delivery sensor is configured to be activated by at least one protrusion on a distal end of the release member when the release member performs the distal movement.

According to an embodiment of the present invention, the at least one start of delivery sensor includes one or more in the group of:

at least one mechanical switch configured to be compressed by the distal movement of the release member; and at least one electrical contact configured to be short-circuited by the distal movement of the release member.

According to an embodiment of the present invention, the at least one start of delivery sensor is configured be deactivated by a proximal movement of the release member, the proximal movement of the release member being initiated by a proximal movement of the activator member.

According to an embodiment of the present invention, the at least one information communication unit includes at least one information indication arrangement.

According to an embodiment of the present invention, the information includes one or more in the group of:

at least one visual indication which indicates that the medicament delivery is in progress;

at least one audible indication which indicates that the medicament delivery is in progress;

at least one tactile indication which indicates that the medicament delivery is in progress;

at least one visual indication which indicates that the medicament delivery has ended;

at least one audible indication which indicates that the medicament delivery has ended;

at least one tactile indication which indicates that the medicament delivery has ended;

at least one visual indication which indicates that a predetermined time period has lapsed after the medicament delivery ended;

at least one audible indication which indicates that a predetermined time period has lapsed after the medicament delivery ended;

at least one tactile indication which indicates that a predetermined time period has lapsed after the medicament delivery ended; and an audible instruction which explains how the medicament delivery device should be handled.

According to an embodiment of the present invention, the at least one information indication arrangement includes one or more in the group of:

at least one light source configured to emit light as an indication;

at least one loudspeaker configured to emit an audible indication; and at least one tactile indication generating member.

According to an embodiment of the present invention, the at least one information communication unit includes at least one transmission unit configured to provide a wireless transmission of the information to at least one external receiving device.

According to an embodiment of the present invention, the information is based on preconfigured data and/or on measured data related to the medicament delivery, the data including one or more in the group of:
- an identification number for the medicament delivery device;
- an identification number for a medicament being delivered by the medicament delivery device;
- an identification number for a patient using the medicament delivery device;
- an elapsed time since a delivery of a medicament occurred;
- at least one indication of that the medicament delivery is in progress;
- at least one indication of that the medicament delivery has ended; and
- at least one indication of that a predetermined time period has lapsed after the medicament delivery ended.

According to an embodiment of the present invention, the electrical information device is included within a housing of the medicament delivery device.

According to an embodiment of the present invention, the electrical information device is included in an external unit, the external unit being releasably attachable to the medicament delivery device.

According to an aspect of the present invention, the object is also achieved by the above mentioned medicament delivery device according to the characterizing portion of claim 15. The medicament delivery device includes an electrical information device according to any one of the above described aspect and/or embodiments; and one or more of:
- at least one release member including least one protrusion on its distal end, the at least one protrusion being configured to activate the at least one start of delivery sensor of the electrical information device if the at least one release member moves distally;
- at least one guide rod member arranged within at least one end of dose signaling member, the at least one guide rod member including at least one protrusion on its distal end, the at least one protrusion being configured to activate at least one end of delivery sensor of the electrical information device if at least one guide rod member moves distally;
- at least one end of dose signaling member including at least one protrusion on its distal end, the at least one protrusion being configured to activate at least one end of delivery sensor of the electrical information device if the end of dose signaling member moves distally; and
- at least one release member returning spring configured to move the release member proximally if the activator member moves proximally.

Also, the medicament delivery device may include one or more of the below described parts of a medicament delivery device.

The above and below mentioned units and arrangements, such as e.g. the at least one information communication unit, the at least one activation unit, the at least one information indication arrangement and/or the at least one transmission unit, can be at least partly implemented in a computer program, which, when it is executed in a processor, instructs the processor to execute the steps taken by the units and arrangements, respectively. The computer program is often constituted by a computer program product stored on a non-transitory/non-volatile digital storage medium, in which the computer program is incorporated in the computer-readable medium of the computer program product. Said computer-readable medium comprises a suitable memory, such as, for example: ROM (Read-Only Memory), PROM (Programmable Read-Only Memory), EPROM (Erasable PROM), Flash memory, EEPROM (Electrically Erasable PROM), a hard disk unit, etc.

Here and in this document, the arrangements and/or units are often described as being arranged for performing steps according to the invention. This also includes that the arrangements and/or units are designed to and/or configured to perform these steps. For example, these arrangements and/or units can at least partly correspond to groups of instructions, which can be in the form of programming code, that are input into, and are utilized by, the processor when the units and/or arrangements are active and/or are utilized for performing its step, respectively.

Detailed exemplary embodiments and advantages of the communication device according to the invention will now be described with reference to the appended drawings illustrating some preferred embodiments.

BRIEF DESCRIPTION OF THE DRAWINGS

Embodiments of the invention are described in more detail with reference to attached drawings illustrating examples of embodiments of the invention in which:

FIGS. 7a-b show parts of a medicament delivery device and an electrical information device according to some embodiments of the present invention.

DETAILED DESCRIPTION OF INVENTION

In the following, the present invention is often exemplified as implemented in an automatic or semi-automatic injection device, such as the one disclosed in WO2014154490. The present invention can, however, be implemented in essentially all kinds of medicament delivery devices that include at least one physical part corresponding to the below described release member which moves when the medicament delivery to the patient starts, and is thus not restricted to implementation in automatic or semi-automatic injection devices.

Figure 1:
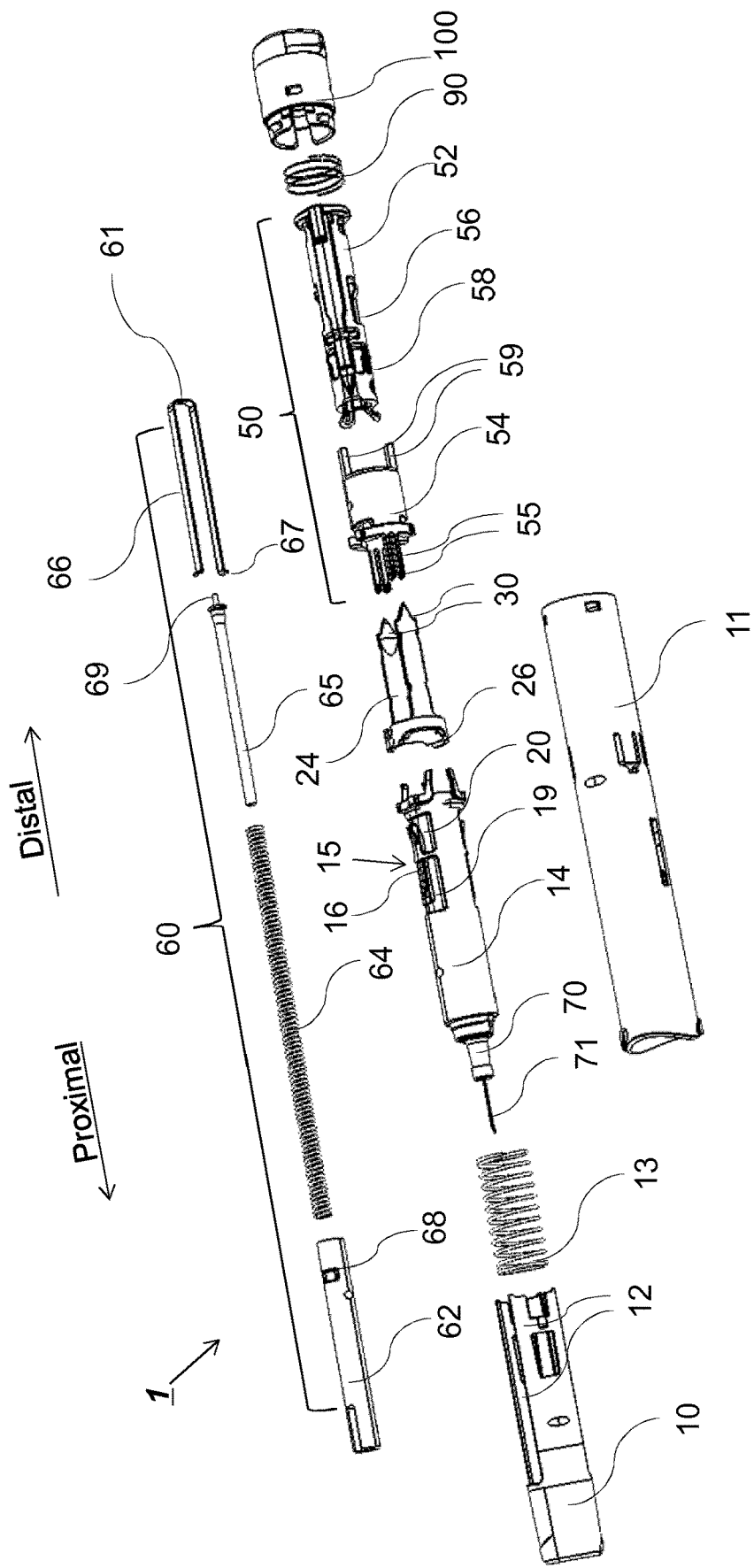
FIG. 1 shows some parts of a medicament delivery device.

FIG. 1a shows an exploded view of some parts of a medicament delivery device 1 according to some embodiments of the present invention, in which the electrical information device according to the present invention can be implemented. For reasons of visibility, FIG. 1 shows some, not all, parts of the medicament delivery device. A medicament delivery device includes a large number of internal parts. In this document, however, only the parts of a medicament delivery device being useful for understanding the present invention are described. For example, the housing of the device is only partially disclosed, since it would otherwise cover the internal parts of the device. In the figures, corresponding parts of the device have been given the same reference numerals.

In this document, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

The medicament delivery device 1 comprises an activator member 10, for example a needle guard, or a sleeve-like structure being slidable/movable in the longitudinal/axial direction inside a generally cylindrical housing 11. In this document, the activator member 10 is often described as a needle guard. However, essentially any part of the medicament delivery device performing a similar movement as the needle guard when the medicament delivery device is used can be used as the activator member 10 according to the embodiments described herein. A spring 13 may be arranged for urging the needle guard 10 in the proximal direction.

The needle guard 10 may comprise a generally tubular part at its proximal end, and at least one distally directed leg 12. For example, the needle guard 10 may comprise at least two distally directed legs 12 extending from the proximal tubular part. Further, the legs 12 can have two tongues extending in the distal direction from opposite sides thereof. At or near the distal end of the two tongues, a bridge connecting the two tongues can be provided. A medicament container holder 14 arranged for holding a medicament container 70 may be arranged inside the needle guard 10. The medicament container 70 may comprise a medicament delivery member. However, the medicament delivery member does not have to be part of the medicament container and may be an independent element of the device. As is exemplified in FIG. 1, the medicament delivery member may be a needle 71. A side surface of the medicament container holder 14 may be arranged with a locking mechanism 15. The locking mechanism 15 of the embodiment comprises a lever. The lever may for example have the form of a longitudinally extending beam 16. The beam 16 may be connected at the middle thereof to the medicament container holder 14 by two pivot arms having a proximal end 19 and a distal end 20. The beam 16 may be formed integral with the medicament container holder 14 or pivotally engaged therewith. The distal end 20 of the beam 16 may be arranged with an outward protrusion. Preferably, the protrusion as a proximal side surface, a surface facing towards the proximal end of the device, forming an acute angle with the longitudinal direction. The needle guard 10 may be in such an arrangement with respect to the beam 16 that the two tongues 12 are positioned, when the device is assembled, on each side of the beam 16 without overlapping. The medicament container holder 14 may have at least one arm on an outer surface thereof.

Furthermore, the device may be provided with an activator 24. The activator 24 may comprise a generally ring-shaped or sleeve-shaped part 26 surrounding the medicament container holder 14 and positioned distally in relation to the needle guard 10. The ring-shaped part 26 may have at least one distally directed activation leg 30, preferably two legs on opposite sides. The legs 30 may have pointed distal ends, which are arranged to wedge in between a pair of lock arms 55 of a release member 54 by making a sliding movement in the distal direction during the activation of the device when the needle guard is forced distally. The release member 54 may for example have the form of a release sleeve.

At the distal direction of the activator 24 is arranged a drive holder, e.g., an injection drive holder 50, for releasably holding a drive, e.g., an injection drive 60, in a pre-tensioned state before injection of the medicament. The injection drive holder 50 may comprise a tubular extension part 52 and a release member 54 coaxially arranged thereon. The tubular extension part 52 accommodates at least a part of the injection drive 60 therein to be axially movable. In order to hold the injection drive 60 in place, the tubular extension part 52 comprises at least one release hook 56, preferably two on opposite sides, arranged on an outer surface thereof. The release hook 56 is flexible and can be pressed inward by the release member 54 when the release member 54 rides thereon, thereby locking the injection drive 60 in place before injection of the medicament. At the outer surface of the tubular extension part 52 is arranged at least one slot 58, preferably two slots at opposite sides, for engaging with, and locking, the release member 54.

Further, the release member 54, surrounding the tubular extension part 52, is axially movable along the outer surface of the tubular extension part 52 when it is not locked with the slot 58 on the tubular extension part 52. The release member 54 may comprise a generally tubular distal part arranged with at least one pair of lock arms 55, preferably two pairs on opposite sides, extending in the proximal direction. The two lock arms 55 forming one pair have a small interval between them running in the longitudinal direction. The interval can be of any size as long as the pointed end of the activator leg 30 can wedge in therethrough when the activator 24 is forced distally by the needle guard 10. Further, each one of the lock arms 55 has a radially inward protrusion which can engage with the slot 58 formed on the tubular extension part 52 to lock the longitudinal movement of the release member 54.

The injection drive 60 may comprise a plunger member or an elongated plunger rod 62. The plunger member may be provided with a hollow space into which a drive spring 64 is arranged to spring-load the rod plunger member 62. The proximal end of the elongated plunger rod 62 may be in contact with a stopper of the medicament container 70. A supporting guide rod member 65 is arranged within the drive spring 64. The guide rod 65 may be provided with at least one protrusion 69 on its distal end, which is described more in detail below. A distal end of the drive spring 64 may be in contact with an end of dose signaling member 66, e.g. a bracket 66 possibly having a general elongated U-shape and longitudinally directed legs, and being arranged for holding the drive spring 64. Each one of the legs may here include a radial outwardly extending ledge 67. The end of dose signaling member 66 may be configured to at least partially surround the spring-loaded plunger member 62. The end of dose signaling member 66 may be provided with a hole 61, in which the at least one guide rod protrusion 59 may be inserted, which is described more in detail below.

When the injection drive 60 is in the pre-tensioned state, the distal end of the end of dose signaling member 66, e.g. of the drive spring holder bracket, is arranged at a predetermined distance from an inner distal surface of said tubular extension part 52 and when the injection drive 60 is released, the end of dose signaling member 66 and the supporting guide rod member 65 are moved distally towards the tubular extension part 52 by a remaining force exerted by the drive spring 64.

When the medicament delivery drive unit is assembled, the drive spring 64 may be compressed between a proximal inner end surface of the plunger member 62 and a transversal contact end of the end of dose signaling member 66. The radial outwardly extending ledges of proximal end 67 of the end of dose signaling member 66 may be engaged with the proximal annular surface of the tubular extension part 52 for preventing the end of dose signaling member 66 from being moved in the distal direction by the force exerted from the drive spring 64. The release member 54 may be arranged for surrounding the tubular extension part 52 at a (proximal) position where the at least one pair of lock arms 55 of the release member 54 engage with the slot 58 on the tubular extension part 52. At this position, the release hook 56 of the tubular extension part 52 is pressed inward by an overlapping inner surface of the release member 54 so as to engage with a groove, e.g., cut-out 68, formed on an outer circumference of the plunger rod 62, thereby preventing longitudinal movement of the injection drive 60 before activation of the device.

In the initial state, since the lock arms 55 of the release member 54 are engaged with the slot 58 on the tubular extension part 52 through their inward protrusions, axial movement of the release member 54 is prevented. At the same time, since the release member 54 at this position presses the release hooks 56 inwardly, the tubular extension part 52 locks the plunger rod 62 in place. Also, the needle guard 10 and the activator 24 are also in their initial position, whereby the activator 24 is inhibited from distal movement. This holding of the activator 24 secures the locking between the release member 54 and the tubular extension part 52.

A medicament dose delivery is performed by pressing the proximal end of the needle guard 10 against a dose delivery site, e.g. a tissue of a body part of a patient. This causes/forces the needle guard 10, together with the activator 24, to slide in the distal direction of the medicament delivery device 1. By this distal movement, the distally directed legs 30 of the activator 24 move distally into the small interval between the pair of lock arms 55 of the release member 54. As the activator 24 slides further distally, the pointed end of the activator legs 30 wedge in between the pairs of lock arms 55. This forces the lock arms 55 to opposite sides of the slot 58, and finally disengages them from the slot 58. After this, further distal movement of the activator 24 can push the release member 54 toward the distal end of the device. When the release member 54 is moved a specified distance in the distal direction, it leaves the release hooks 56 of the tubular extension part 52 that have been pressed in to hold the injection drive 60. As the release hooks 56 move outwards, the injection drive 60, i.e., the plunger rod 62 and the drive spring 64 in the pre-tensioned locked state, is released from the locked state. The plunger rod 62 may then be forced in the proximal direction by the drive spring 64 and may act on the stopper inside the medicament container 70 so as to deliver a dose of medicament through the medicament delivery member at the dose delivery site. Thus, delivery of a dose of medicament is initiated.

During the medicament delivery procedure, when the distal end of the plunger rod 62 passes by the end of dose signaling member 66, i.e. when the plunger rod 62 passes by the proximal end 67 of the of the end of dose signaling member 66, and thereby passes the radial outwardly extending ledges, the end of dose signaling member 66 is released and is allowed to move in the distal direction by a remaining force exerted by the drive spring 64.

When the stopper has reached its end position, i.e. the proximal end position, inside the medicament container 70, the medicament delivery operation is completed. Upon the completion of the delivery, the device may be withdrawn from the dose delivery site. This in turn may cause the needle guard 10 to be moved in the proximal direction by the spring 13. The proximal movement by the spring 13 will cause the needle guard 10 to release the proximal end 19 of the beam 16 which has been pressed inward during the injection operation by the overlapping part of the needle guard 10. Thus, the proximal end 19 of the beam 16 will flex outwards in the radial direction due to the tension built up in the beam 16 by the protrusion at the distal end 20 being kept pressed inwards by the activator 24. The lever, preferably the beam 16, may thus reach the final position, in which the lever restricts the movement of needle guard 10 in the distal direction. The device 1 may also, according to an embodiment, include at least one release member returning spring 90 configured to move the release member 54 proximally if the needle guard 10 moves proximally, as is described more in detail below.

In FIGS. 2-6 described below, not all part of the devices are described for each figure. However, corresponding descriptions for the parts with the same reference numerals can be found above for FIG. 1.

According to an aspect of the present invention, an electrical information device 100 configured to communicate information related to a medicament delivery performed by a medicament delivery device is presented. An electrical information device 100 according to the present invention and/or according to some embodiments of the present invention is disclosed in FIGS. 2a-b.

The electrical information device 100 includes at least one start of delivery sensor 101 configured to detect a distal axial movement of the release member/sleeve 54 of the medicament delivery device 1. The release member 54 is, as described above, configured to be distally moved when a needle guard 10 of the medicament delivery device 1 is forced distally. This typically happens when the medicament delivery device 1 is pressed against a dose delivery site, such as a body part, in order to deliver the medicament to a patient.

The electrical information device 100 also includes at least one information communication unit 110, which is configured to communicate information related to the medicament delivery. According to different embodiments described below, the at least one information communication unit 110 may also include at least one information indication arrangement 130 and/or at least one transmission unit 140.

The electrical information device 100 further includes at least one activation unit 120, which is configured to activate the at least one information communication unit 110 based on a detected distal axial movement of the release member 54. Thus, when the medicament delivery device 1 is pressed against a dose delivery site, the needle guard 10 of the medicament delivery device 1 is forced distally, which moves the release member 54 distally. The distal movement of the release member 54 is detected by the at least one start of delivery sensor 101, and the at least one information communication unit 110 is then woken up by the at least one activation unit 120.

Figure 2A:
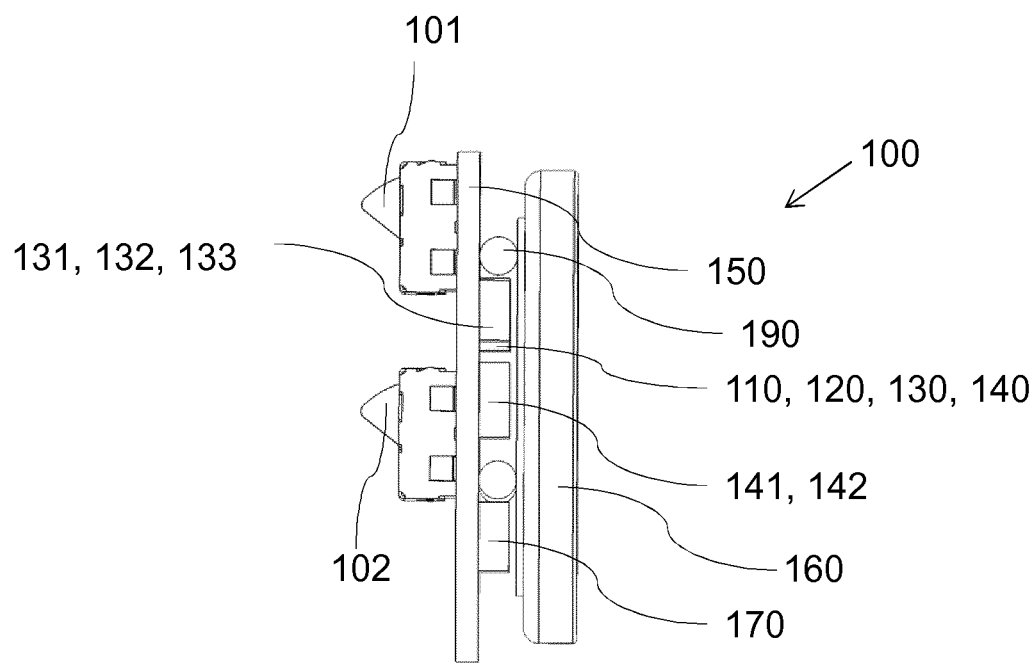
FIGS. 2a-b show details of an electrical information device according to some embodiments of the present invention.
Figure 2B:
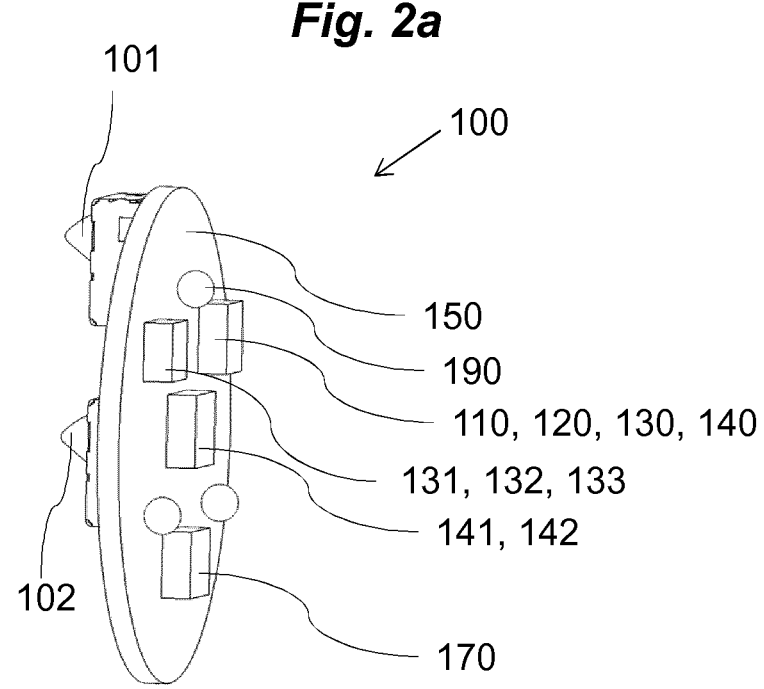

As illustrated e.g. in FIGS. 2*a-b*, the electrical information device 100 can according to some embodiments include at least one Printed Circuit Board (PCB) 150 and may be driven/provided with electrical power by at least one battery 160 such as e.g. a coin cell battery. The electrical information device 100 may also include one or more spacer elements 190, that can have e.g. an essentially spherical shape, arranged between the at least one PCB 150 and the at least one battery 160. The one or more spacer elements 190 create a space between the at least one PCB 150 and the at least one battery 160, such that components might be attached on both sides of the at least one PCB 150. Also, the at least one spacer may be electrically conducting, and may thus be used for electrically connecting the at least one battery 160 to the at least one PCB 150.

In FIGS. 2*a-b*, the at least one information communication unit 110, the at least one activation unit 120, the at least one information indication arrangement 130, and the at least one transmission unit 140 are illustrated as being included in one circuit, which e.g. can be a processor executing instructions corresponding to these units, as mentioned above. However, as understood by a skilled person, these units may also be included in two or more circuits, e.g. two or more such processors.

According to different embodiments of the present invention, the at least one activation unit 120 is configured to activate the at least one information communication unit 110 based on the detected movement. According to an embodiment, the whole electrical information device 100 is activated by the at least one activation unit when a movement of the release member 54 is detected.

The electrical information device 100 according to the present invention can be implemented within the housing 11 of the medicament delivery device 1, e.g. by at least partly exchanging the end assembly at the distal end of the medicament delivery device 1 with an end assembly including the electrical information device 100.

The present invention facilitates for taking a prescribed dose of a medicament, and also makes an automated and reliable monitoring of whether patients follow their prescribed medication schemes possible. Hereby, the present invention can thus be used for reducing the suffering for the patient, and also the total costs for the medicaments and medical care.

Figure 3A:
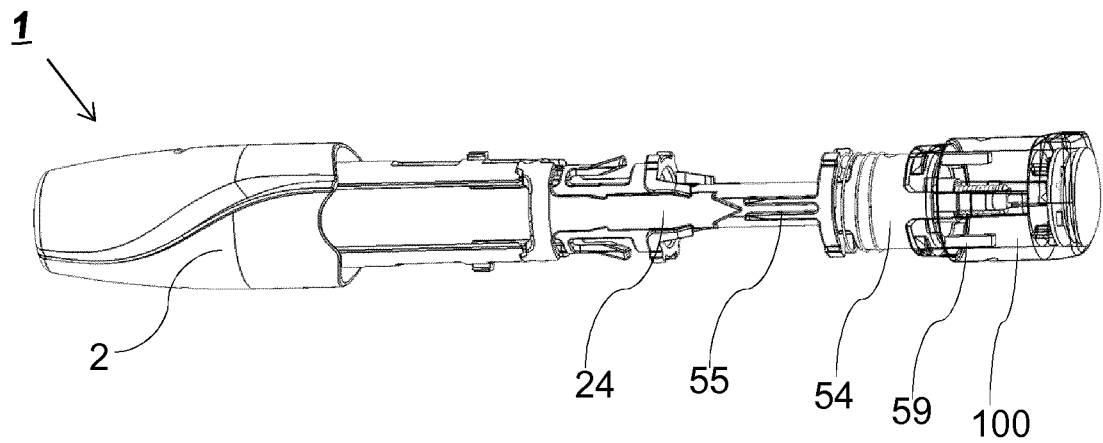
FIGS. 3a-c show parts of a medicament delivery device and an electrical information device according to some embodiments of the present invention for an initial state.
Figure 3B:
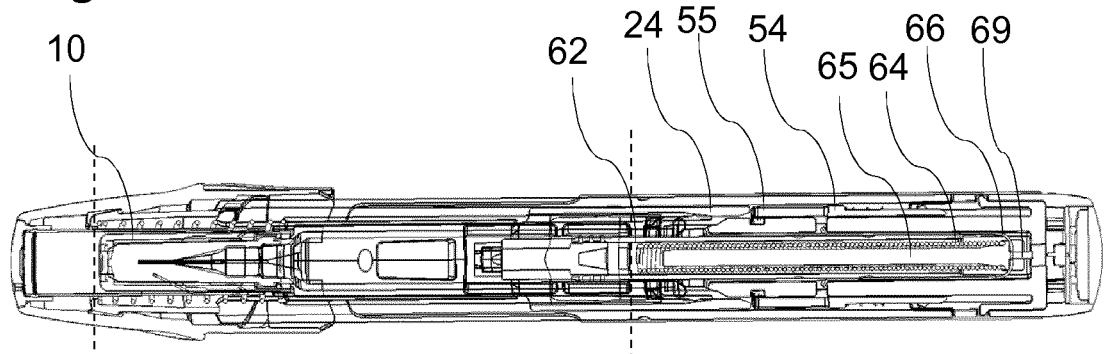
Figure 3C:
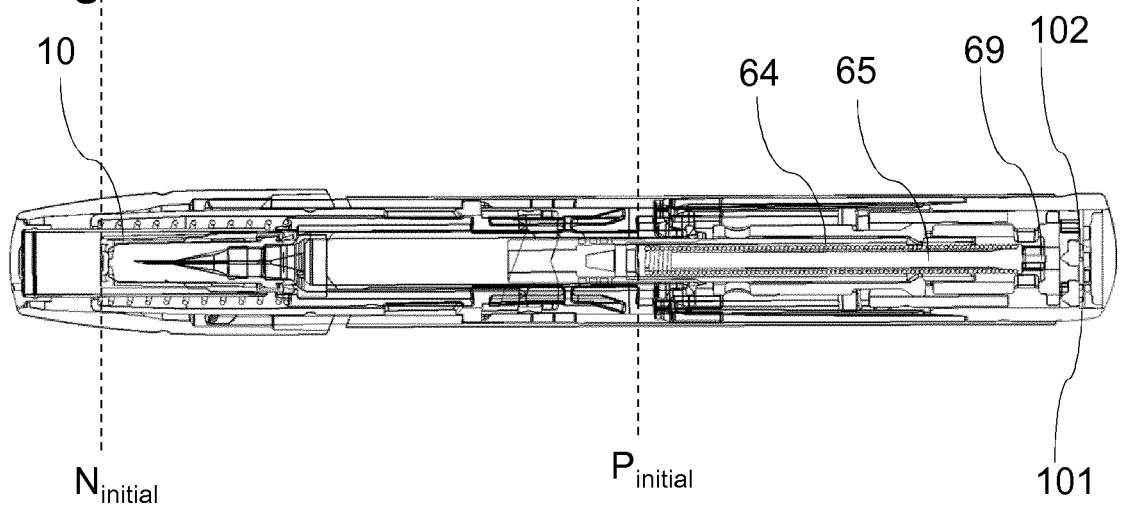

FIGS. 3*a-c* illustrate different views of a medicament delivery device 1 and an electrical information device 100 according to some embodiment of the present invention for an initial state, i.e. before the delivery of the medicament has been performed.

As can be seen in FIGS. 3*a-c*, the medicament delivery device 1, has not yet been pressed against a dose delivery site, and the needle guard 10 is in its initial position $N_{initial}$. Also, the plunger rod 62 is in its initial position $P_{initial}$.

FIGS. 4*a-d* illustrate different views of a medicament delivery device 1 and an electrical information device 100 according to some embodiments of the present invention for a delivery state, i.e. after the delivery has started and during which the delivery of the medicament is performed.

The at least one start of delivery sensor 101 is configured to be activated by at least one protrusion 59 on a distal end of the release member 54 when the release member 54 performs a distal movement as the needle guard 10 is forced distally. The needle guard is typically pressed distally when the medicament delivery device 1 is pressed against a dose delivery site.

Figure 4A:
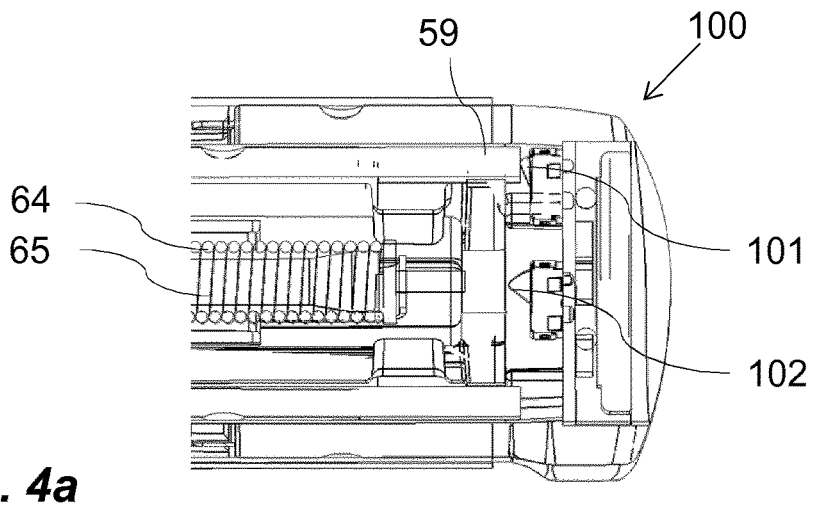
FIGS. 4a-d show parts of a medicament delivery device and an electrical information device according to some embodiments of the present invention for a medicament delivery state.
Figure 4B:
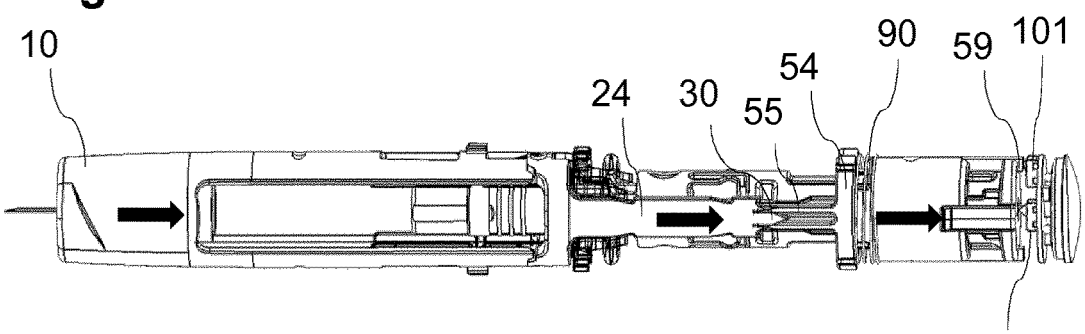
Figure 4C:
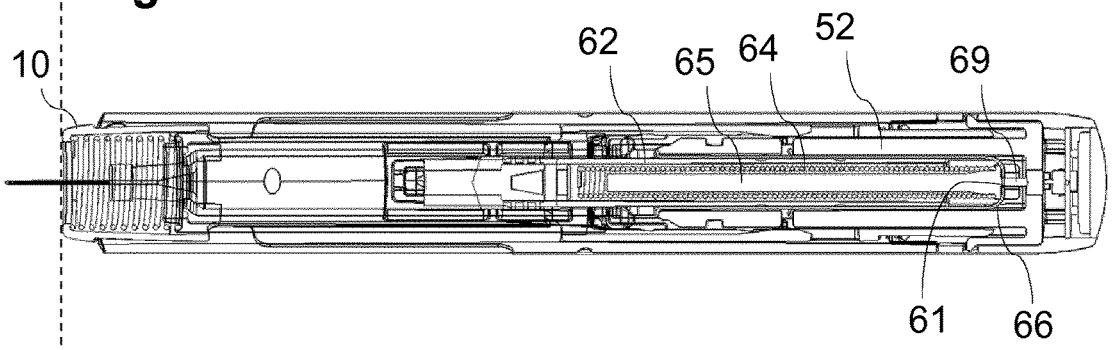
Figure 4D:
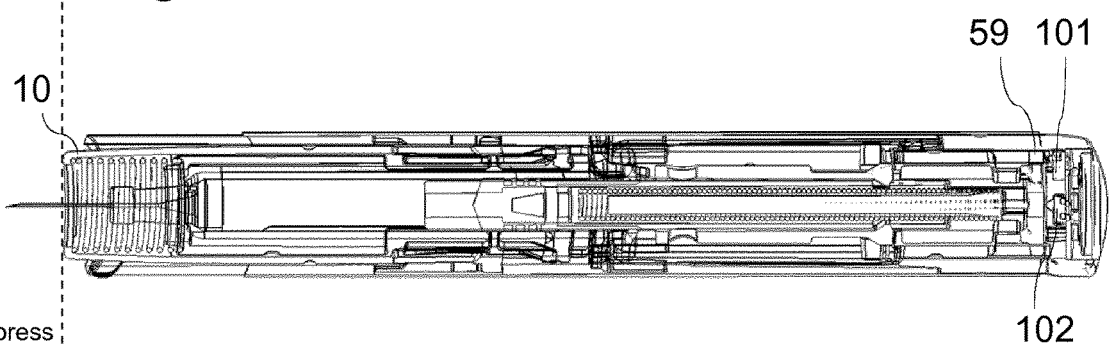

The at least one start of delivery sensor 101 can, according to an embodiment illustrated in FIGS. 4*a-b*, include at least one mechanical switch 101 configured to be compressed by the distal movement of the release member 54, more in detail by the at least one protrusion 59 of the release member 54. According to an embodiment, the at least one start of delivery sensor 101 can include at least one electrical contact 101 configured to be short-circuited by the distal movement of the release member 54, e.g. by at least one first contact element arranged on the protrusion 59 and at least one second contact element arranged on the PCB 160, wherein the first and second contact elements are pressed together to make contact when the release member 54 moves distally.

Thus, when the medicament delivery device 1 is pressed against a dose delivery site, the needle guard 10 of the medicament delivery device 1 is forced distally $N_{press}$ from its initial position $N_{initial}$ to its delivery position $N_{del}$, which moves the release member 54 distally (indicated with an arrow in FIG. 4*b*). The distal movement of the release member 54 is detected by the at least one start of delivery sensor 101 since the protrusion 59 of the release member 54 presses against the at least one start of delivery sensor 101, and the at least one information communication unit 110 is then woken up by the at least one activation unit 120.

After the delivery of the medicament has started, the medicament container 70 is emptied during the medicament delivery.

FIGS. 5*a-d* illustrate different views of a medicament delivery device 1 and an electrical information device 100 according to some embodiments of the present invention for an end of delivery state, i.e. for at time period after the delivery has been performed.

The electrical information device 100 can, according to an embodiment, include at least one end of delivery sensor 102 configured to detect a predetermined proximal axial movement of a plunger rod 62 (indicated by an arrow in FIG. 5*c*) from its initial position $P_{initial}$ to an end position $P_{end}$. The predetermined proximal axial movement has hereby a length $L_{pre}$ corresponding to a completed delivery of the medicament from the container 70. Thus, the plunger 62 is moved in a proximal direction when the medicament is delivered, and when the plunger 62 has moved the predetermined length $L_{pre}$, this movement is detected by the at least one end of delivery sensor 102. The end of dose delivery sensor 102 can e.g. be arranged essentially centrally on the PCB 150, as shown in FIGS. 2*a-b*.

As mentioned above, the end of dose signaling member 66, e.g. being a u-shaped bracket, is configured to lose its support from the plunger rod 62 when the plunger rod 62 has moved the predetermined length $L_{pre}$ proximally from its initial position $P_{initial}$ to the end position $P_{end}$. Hereby, the end of dose signaling member 66 is configured to be released from its initial fixed position, which it has up until the delivery is ended. When the end of dose signaling member 66 is released, it performs an axial distal movement, i.e. towards the distal end of the medicament delivery device 1. When the end of dose signaling member 66 is released, also at least one guide rod member 65 arranged within the end of dose signaling member 66 moves distally (as indicated with an arrow in FIG. 5*c*). The distal movement of the end of dose signaling member 66 and/or the at least one guide rod member 65 is detectable by the end of delivery sensor 102.

The end of delivery sensor 102 can, according to an embodiment, include at least one mechanical switch 102, which is configured to be compressed by a distal movement of the end of dose signaling member 66 and/or the at least one guide rod member 65. The end of delivery sensor 102 can, according to an embodiment, include at least one electrical contact 102 configured to be short-circuited by a distal movement of the end of dose signaling member 66 and/or the at least one guide rod member 65.

Figure 5A:
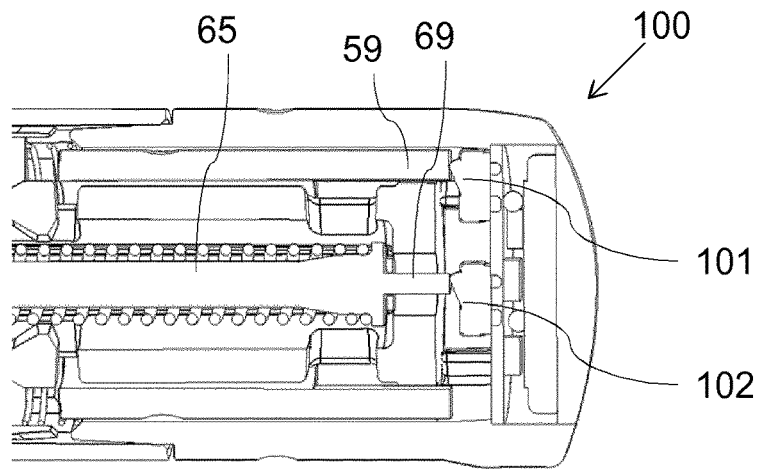
FIGS. 5a-d show parts of a medicament delivery device and an electrical information device according to some embodiments of the present invention for an end of delivery state.
Figure 5B:
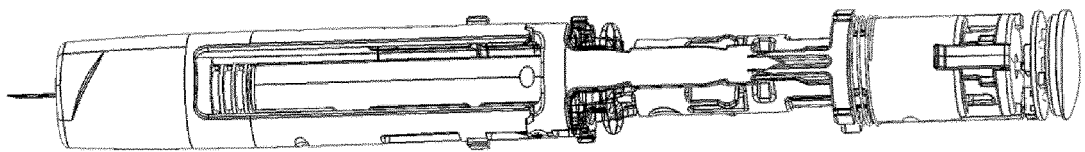
Figure 5C:
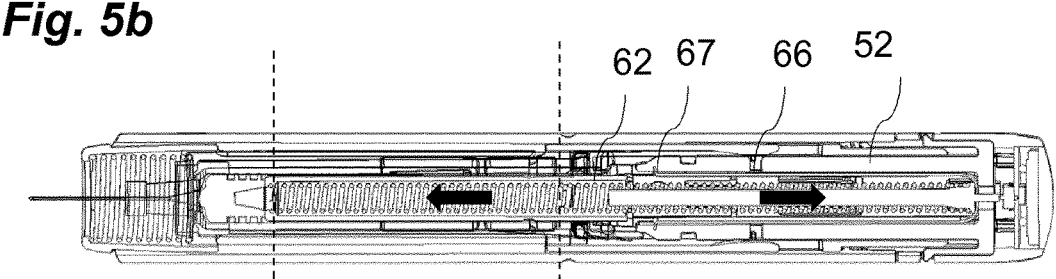
Figure 5D:
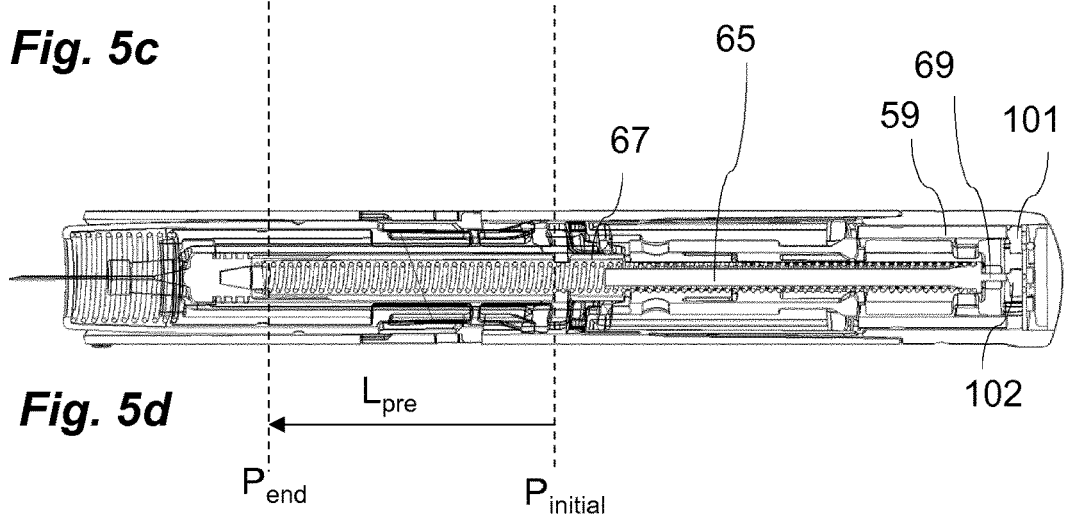

The guide rod 65 may be provided with at least one protrusion 69 on its distal end, as mentioned above. According to an embodiment of the present invention, the at least one protrusion 69 activates the at least on end of delivery sensor 102. For example, the at least one protrusion 69 may press against the at least one end of delivery sensor 102, as is shown in FIGS. 5a-d. The at least one protrusion 69 may e.g. extend through a hole 61 in the distal end of the end of dose signaling member 66 such that it can reach the at least one end of delivery sensor 102. As can be seen in FIGS. 5a and 5d, the start of delivery sensor 101 is here normally still activated/pressed by the at least one protrusion 59 of the release member 54.

According to an embodiment of the present invention, the end of dose signaling member 66 may include at least one protrusion on its distal end. This at least one protrusion is configured to press against, and thereby also activating, the at least one end of delivery sensor 102 when a distal movement of the end of dose signaling member 66 occurs.

When the electronical information device 100 includes both at least one start of delivery sensor 101 and at least one end of delivery sensor 102, also monitoring of the function of the medical delivery device 1 can be performed. For example, the detected delivery time period $T_{del}$ between activation of the at least one start of delivery sensor 101 and activation of the end of delivery sensor 102 can be analyzed. If the delivery time period $T_{del}$ is shorter than a nominal/expected value, this can e.g. be interpreted as the medicament has not been injected into tissue, which may generate an error code/message. On the other hand, if the delivery time period $T_{del}$ is longer than expected, this can e.g. be interpreted as a device malfunction and/or a device fabrication defect. For example, jamming and/or stalling of one or more parts of the medicament delivery device might cause a prolonged delivery time period $T_{del}$.

The usage of both at least one start of delivery sensor 101 and at least one end of delivery sensor 102 according to some embodiments of the present invention also makes it possible to allow greater tolerances, i.e. allow more inexactness, for some parts of the medicament delivery device 1, such as for a diameter of the needle and/or for silicone layers applied on parts within the device.

For example, the inside surface of the container 70, the stopper, and possibly also other parts, can be provided with a silicone layer to reduce friction to other parts. The friction might change over time for these parts, which might also have an impact on the delivery time period $T_{del}$. When the at least one end of delivery sensor 102 is activated, it can be concluded that the medicament has been delivered, and that a predetermined extra time period needed for the medicament to be absorbed in the tissue then starts to run. The prolonged delivery time period does for these embodiments thus not affect the absorption of the medicament, which could be the case if the device 1 would not have an end of delivery sensor 102. Without the at least one end of delivery sensor 102, there would be a risk that the patient would believe that the medicament had been delivered and/or absorbed much earlier than it actually is delivered and/or absorbed, since the only available time indication would then be the start of the delivery, from which the patient would have to count the elapsed time.

According to an embodiment of the present invention illustrated in FIGS. 6a-e, the at least one start of delivery sensor 101 is further configured be deactivated by a proximal movement of the release member 54, whereby the at least one start of delivery sensor 101 is depressed by the movement. As described above, the at least one protrusion 59 of the release member 54 can be used for activating/pressing the at least one start of delivery sensor 101. Thus, when the release member 54 and/or the at least one protrusion 59 move proximally, the at least one start of delivery sensor 101 is depressed/deactivated. The proximal movement of the release member 54 and/or the at least one protrusion 59 can be initiated by a proximal movement of said needle guard 10, e.g. by a reduced proximal pressing force on the medicament delivery device 1.

Figure 6A:
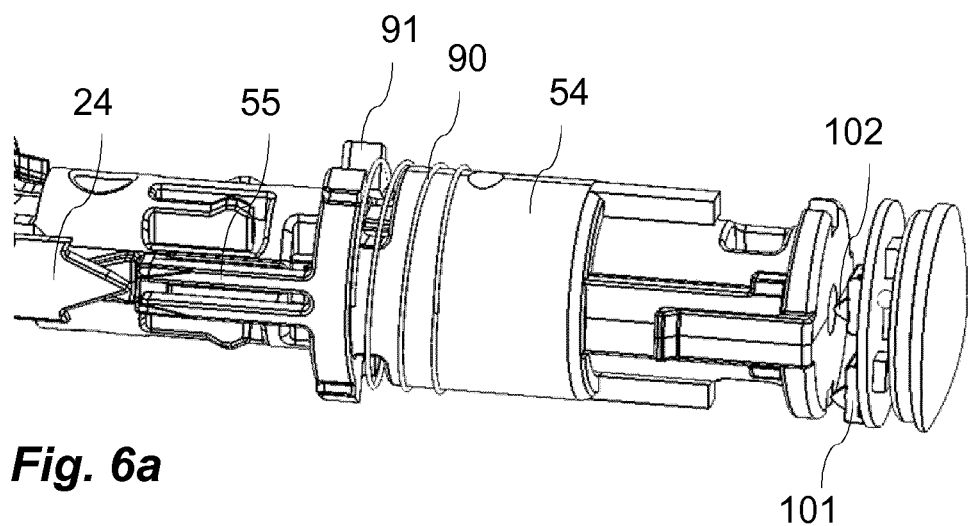
FIGS. 6a-e show parts of a medicament delivery device and an electrical information device according to some embodiments of the present invention for a usage sequence.

According to an embodiment of the present invention, the medicament delivery device 1 includes at least one release member returning spring 90, which is configured to move the release member 54 proximally if the needle guard 10 moves proximally. The release member returning spring 90 can be arranged on the outside of the release member 54, with its proximal end against a sleeve 91 of the release member 54. The distal end of the release member returning spring 90 is arranged against a proximal end 112 of a housing 111 of the electrical information device 100, as shown in FIG. 6e.

As described above, in the initial state disclosed in FIG. 6a, the needle guard 10 and the activator 24 are also in their initial position, whereby the activator 24 is inhibited from distal movement.

Figure 6B:
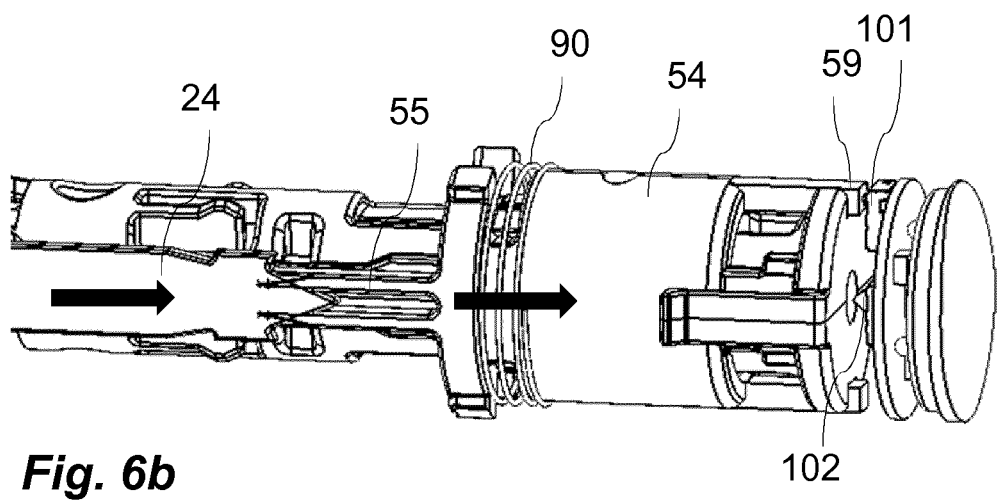

A medicament dose delivery is then performed by pressing the needle guard 10 against a dose delivery site, which causes/forces the needle guard 10, and the activator 24, to slide in the distal direction, which forces the release member 54 toward the distal end of the device, as is illustrated by arrows in FIG. 6b. The at least one start of delivery sensor 101 is then activated by being pressed e.g. by the protrusion 59 of the release member 54. When the release member 54 is pressed distally, a force is built up in the release member returning spring 90 when it is compressed.

Then, the injection drive 60, including e.g. the plunger rod 62 and the drive spring 64, is released, and the plunger rod 62 is forced in the proximal direction so as to deliver a dose of medicament through the medicament delivery member at the dose delivery site. When the distal end of the plunger rod 62 passes by the end of dose signaling member 66, the end of dose signaling member 66, and the guide rod member 65 and its protrusion 69, are released and allowed to move in the distal direction, whereby the end of delivery sensor 102 is activated as shown in FIG. 6c by a remaining force exerted by the drive spring 64.

Figure 6C:
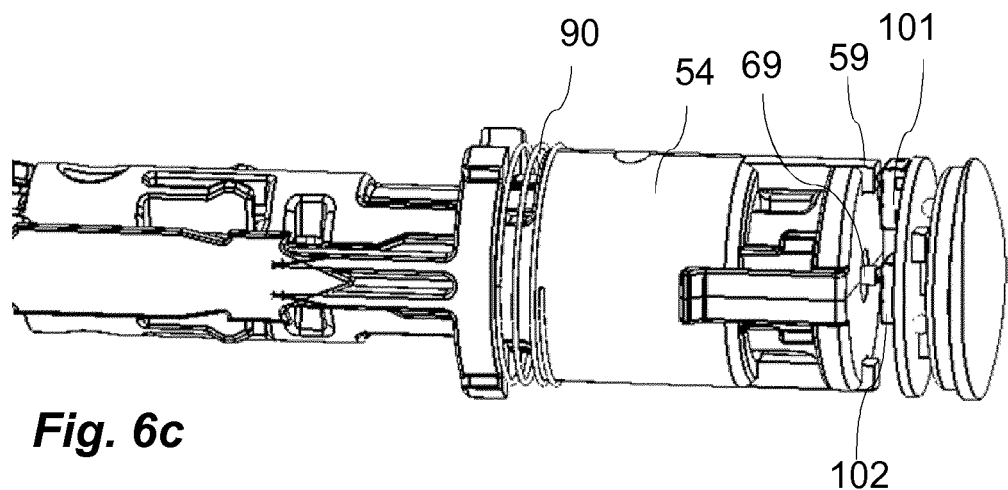

It should here be noted that FIGS. 6a-c illustrate a general medicament delivery process, also for a medicament delivery device not including the release member returning spring 90.

Figure 6D:
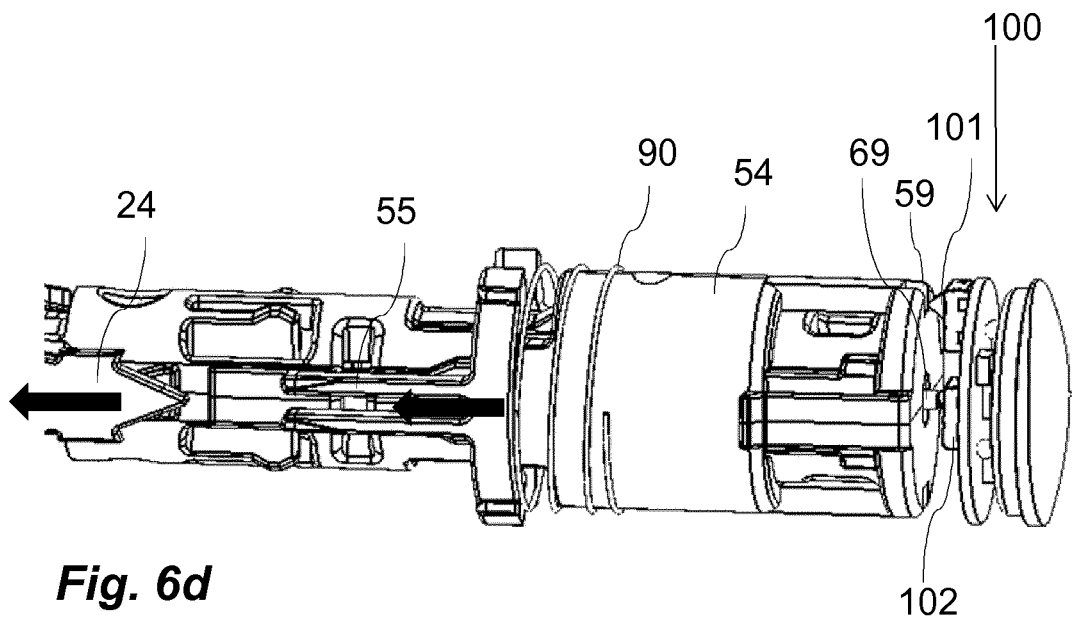
Figure 6E:
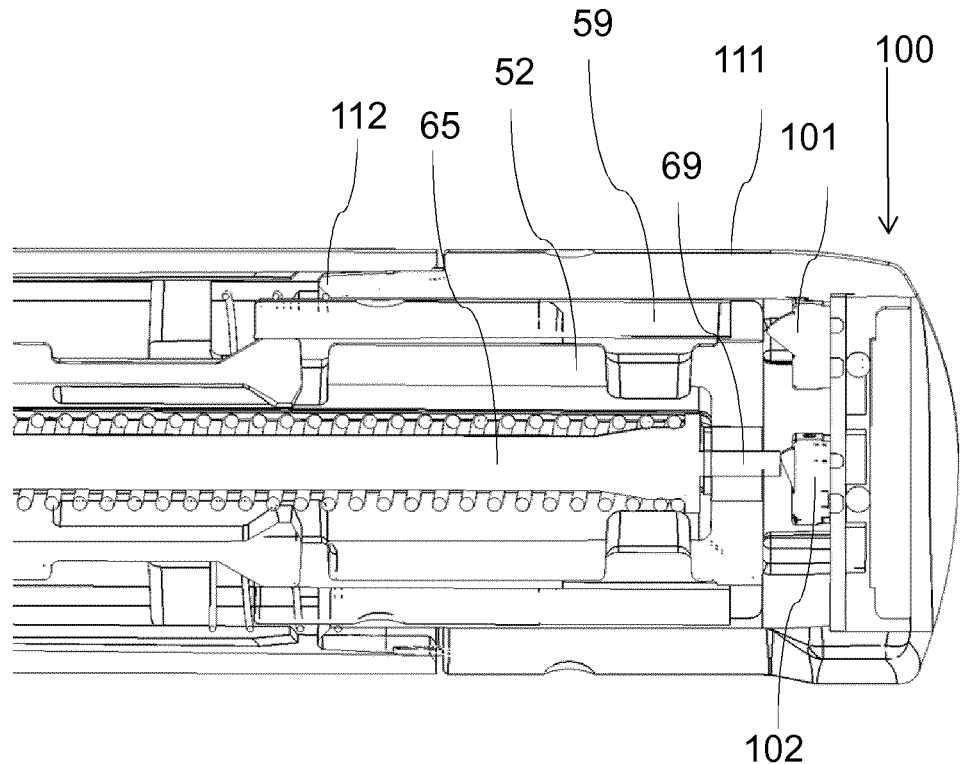

FIGS. 6d-e illustrate the usage principle of the release member returning spring 90. If the needle guard 10 is moved proximally, e.g. by a user reducing the proximal force on the medicament delivery device 1, the activator 24 also moves in a proximal direction.

The needle guard 10 can after the ended delivery e.g. return to its initial position, or can go to a final position, where the final position may be a locked position further proximal than the initial position. Also, the user may during the delivery of the medicament press the device 1 less hard against the delivery site, or may even slightly lift the device 1 from its most proximal position. The needle may then still be in the tissue of the patient, but possibly at a non-optimal depth in the tissue.

The proximal movement of the needle guard 10 makes it possible for also the release member 54 to move in the proximal direction. The force stored in the release member returning spring 90 is then released and the release member 54 is pushed in a proximal direction by the release member returning spring 90. Hereby, also the at least one protrusion 59 of the release member 54 is moved away from the at least one start of delivery sensor 101, which is then deactivated.

Hereby, it is possible to monitor if the needle guard has been pushed to its maximal distal position during the delivery. Thus, it can be monitored if the medicament has been delivered at the intended depth in the tissue or not. If the delivery was performed at a non-optimal depth, a complementary user instruction may be provided to the user, e.g. by an information indication arrangement 130, which is described more in detail below. Also, it can be monitored if the medicament delivery device 1 has been pressed against the tissue during a long enough time in order for the medicament to be totally absorbed by the tissue, i.e. during the delivery time period and also during the predetermined time period after the medicament delivery ended, e.g. 5 seconds.

For prior art devices, lacking the release member returning spring 90, it would be more or less impossible to know if the delivery has been made at the intended depth and/or to determine the actual time period $T_{press}$ the device 1 has actually been pressed against the tissue, since the release member 54 would be stuck in its distal position for the prior art devices.

As described above, the at least one information communication unit 110 is activated by the at least one activation unit 120 if a distal movement of the release member 54 is detected by the at least one start of delivery sensor 101. According to an embodiment of the present invention, the at least one information communication unit 110 includes at least one information indication arrangement 130, which may provide visual indications, audible indications, tactile indications and/or audible instructions.

Such visual indications, audible indications, tactile indications and/or audible instructions may indicate that the medicament delivery is in progress, that the medicament delivery has ended and/or that a predetermined time period has lapsed after the medicament delivery ended. Hereby, the user can be helped to understand the delivery process, and can get more comfortable when using the device 1. Also, by indicating a predetermined time period, for example 5 seconds, has lapsed after the medicament delivery ended it can be secured that the medicament delivery device 1 is held/pressed against the dose delivery site long enough, such that the medicament is completely absorbed by the tissue of the patient, but not un unnecessarily long. Further, an audible instruction, such as e.g. a human or synthesized voice, which explains how said medicament delivery device 1 should be handled can be provided for users in need of extra information and guidance.

The at least one indication arrangement 130 can thus be configured to provide the indication during and/or at the end of a predetermined time period after the delivery has ended. This is possible since the electrical information device 100 is provided with a source of energy, such as a battery, which can be used for providing this prolonged indication, e.g. by letting a LED shine also after the medicament has been delivered. When the medicament delivery device 1 is pressed against the skin of the patient both during the delivery time and during the predetermined time period after the delivery, the medicament being delivered by the medicament delivery device 1 has enough time to be absorbed by the tissue of the patient. The predetermined time period can be set, e.g. depending on the type of drug being delivered.

The at least one information indication arrangement 130 can, according to some embodiments illustrated in FIGS. 2*a-b*, include at least one light source 131, such as a LED, configured to emit light as an indication, at least one loudspeaker 132 configured to emit an audible indication and/or at least one tactile indication generating member 133.

According to an embodiment, the electrical information device 100 also includes at least one clock 170, such as e.g. a clock crystal device, which can be mounted on the PCB 150. The at least one clock 170 can be configured to count a relative time related to the delivery of drugs. Thus, the at least one clock 170 can then count the elapsed period of time from the medicament delivery, such as from the start of the medicament delivery, i.e. from the point in time when the determination unit was activated. Hereby, the clock 170 may be in an off mode until the information communication unit 110 is activated, which saves battery power.

As stated above, for some embodiments of the present invention the device 1 includes both at least one start of delivery sensor 101 and at least one end of delivery sensor 102. For these embodiments, the delivery time period $T_{del}$ is very well defined as the time period between activation of the at least one start of delivery sensor 101 and activation of the at least one end of delivery sensor 102. Therefore, indications and/or instructions related to the medicament delivery can easily be presented exactly during this delivery time period $T_{del}$.

Also, it is very well defined when the medicament delivery has ended, i.e. when the end of delivery sensor is activated, whereby indications and/or instructions related to the predetermined medicament absorption time period $T_{pred}$ can easily be presented exactly during this absorption time period.

Further, it is easily detected if the medicament delivery is not performed at the right depth, or not in the tissue at all, i.e. if the device 1 is not properly pressed against the tissue. This can e.g. be detected if the start of delivery sensor 101 is deactivated before the end of delivery sensor 102 is activated. Hereby, indications and/or instructions related to the medicament delivery depth can be presented when such a problem occurs.

According to an embodiment, the at least one information communication unit 110 includes a wireless transmission unit 141, such as e.g. a Bluetooth transmission unit or a unit transmitting information according to another suitable wireless transmission protocol to an external receiver, such as a cellular or non-cellular transmission protocol. Also, the electrical information device 100 may according to an embodiment include an antenna unit 142 arranged on the at least one PCB 150 in order to transmit the information to the external receiver.

According to an embodiment, the transmission unit 140 is configured to create a connection between the electrical information device 100 and an external receiving device, e.g. a smartphone, a server, a cloud computing device or the like, essentially directly at the activation of the electrical information device 100 and/or the information communication unit 110. The transmission unit 140 can also be configured to transmit various information from the electrical information device 100 to the external receiving device.

Hereby, interactive information may be presented by the smartphone during the medicament delivery.

The information may for example can be based on pre-configured data and/or measured data related to the medicament delivery. Such data may include e.g. an identification number identifying the medicament delivery device, an identification number identifying a medicament/drug being delivered by the medicament delivery device, an identification number identifying a patient using the medicament delivery device, an indication of that the medicament delivery is in progress, an indication of that the medicament delivery has ended, an indication of that a predetermined time period has lapsed after the medicament delivery ended and/or an elapsed time since a delivery of a medicament/drug occurred.

By transmitting the information to the external receiver, a remote and reliable monitoring of whether patients follow their prescribed medication schemes and/or handle the device correctly can easily be performed. Based on this monitoring, e.g. a doctor can identify and contact a patient not following the medication scheme or device handling instructions. The monitoring can help a doctor to find out if a patient needs additional information and/or help with taking the medicaments. Maybe, the doctor could also come to the conclusion that a change of medicament and/or medication scheme should be made in order to increase the compliance of the patient. The present invention can thus be used for lowering the risk for a prolonged sickness/disease/condition and/or for lowering the risk of further complications due to non-optimal medicament intake. Hereby, the suffering for the patient is minimized, and the total costs for the medicaments and medical care are also lowered.

According to an embodiment of the present invention, the electrical information device 100 is included within a housing 2, 11 of the medicament delivery device 1. The housing 2, 11 is for visibility reasons only partly showed in the figures, e.g. in FIGS. 1 and 3a.

According to an embodiment of the present invention, the electrical information device 100 is included in an external unit 700, illustrated in FIGS. 7a-b, which is releasably attachable to the medicament delivery device 1, e.g. to the distal end of the medicament delivery device 1. The electrical information device 700 can, according to an embodiment, be attachable to the medicament delivery device 1 by use of magnetic force. At least one magnetic element 711, such as a magnetic ring, one or more magnets or one or more magnetic metal elements, can then be arranged on the proximal end/surface of the electrical information device 700. On the distal end/surface of the medicament delivery device 1, corresponding at least one magnetic element 712, such as a magnetic ring, one or more magnets or one or more magnetic metal elements, can be arranged. When these magnetic elements 711, 712 are brought close to each other, the magnetic force is created, which releasably holds/secures the electrical information device 700 to the medicament delivery device 1.

Also, one or more guide tabs 713 and/or one or more corresponding guide slots 714 can be arranged at the proximal end/surface of the external electrical information device 700 and/or at the distal end/surface of the medicament delivery device in order to fit the electrical information device 700 into the right position when being attached to the medicament delivery device 1. When being detached from the medicament delivery device 1, the electrical information device 700 can be pulled and/or twisted, whereby its fitted position, provided by the guide tabs 713 and guide slots 714, and also the magnetic force, is lost. A skilled person realizes that essentially any releasable attachment to the medicament delivery device providing a solid attachment can also be used for this attachment, such as e.g. flexible snap fits.

According to an embodiment, the electrical information device 100 includes an attachment switch, which is configured to be activated when the communication device is releasably attached to the medicament delivery device. Thus, the attachment switch is activated when the electrical information device 100 is mounted on the medicament delivery device 1, e.g. by mounting it on the distal end of the medicament delivery device 1 by pressing it against the distal end, thereby enabling activation of the electrical information device 100. Hereby, one or more parts of the electrical information device 100, such as e.g. the at least one start of delivery sensor 101, the at least one information communication unit 110, the at least one activation unit 120, the at least one transmission unit 140, may be activated after the attachment switch has been pressed.

According to an aspect of the present invention, a medicament delivery device 1 is presented. The medicament delivery device includes an electrical information device 100 according to any of the embodiments described herein. The medicament delivery device also includes one or more of:

the above described at least one release member 54 including least one protrusion 59 on its distal end;
the above described at least one guide rod member 65 including at least one protrusion 69 on its distal end;
the above described at least one end of dose signaling member 66 including at least one protrusion on its distal end; and
the above described at least one release member returning spring 90 configured to move the release member 54 proximally if the needle guard 10 moves proximally.

According to an embodiment, the medical delivery device 1 further includes a tubular housing 11 having a proximal end and an opposite distal end, and a drive 60 configured to exert force on a medicament container 70 to expel medicament. The device 1 also includes a drive holder configured to releasably hold the drive 60 in a pre-tensioned state before delivery of the medicament. The drive holder 50 comprises a tubular extension part 52 for receiving the drive 60 to be axially movable therein and a release member/ring 54 coaxially arranged on the tubular extension part, the release member/ring 54 being axially movable between proximal and distal positions along the outer surface of the tubular extension part. Also, the tubular extension part is configured to engage with the drive 60 when the release member/ring is at the proximal position and to release the drive 60 as the release member/ring 54 moves distally leaving the proximal position.

FIGS. 8a-d shows the distal end/surface of the medicament delivery device 1 and the external unit 700.

Figure 8A:
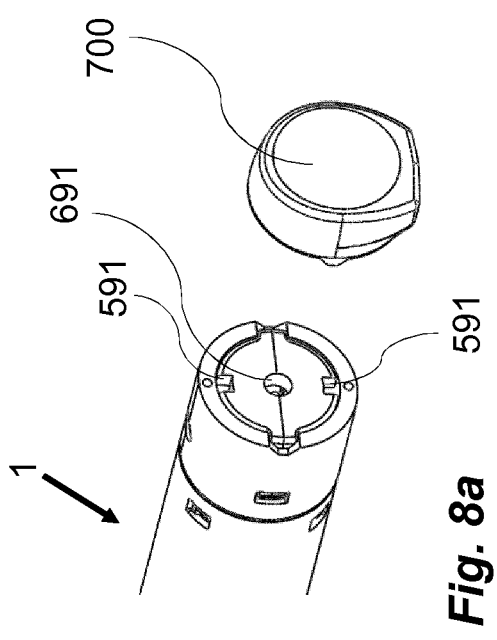
FIGS. 8a-d show parts of a medicament delivery device and an electrical information device according to some embodiments of the present invention for a usage sequence.

As described above, in the initial state disclosed in FIG. 8a, the needle guard 10 and the activator 24 are in their initial position, whereby the activator 24 is inhibited from distal movement. The distal end of the medicament delivery device 1 is provided with one or more holes/openings 591, through which release member protrusions 59 may extend, and/or one or more holes/openings 591, through which signaling member protrusions 69 may extend. In the initial state, however, the protrusions 59, 69 do not extend through these one or more holes/openings 591, 691, as is shown in FIG. 8a.

Figure 8B:
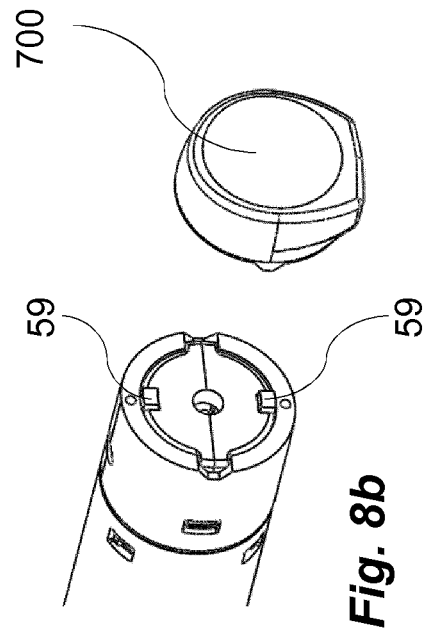

When a medicament dose delivery is performed by pressing the needle guard 10 against a dose delivery site, the needle guard 10 and the activator 24 are forced to slide in the distal direction, which forces the release member 54 and its one or more protrusions 59 distally. Hereby, the one or more protrusions 59 extend through the holes/openings 591 and rises above the distal surface of the medicament delivery device 1, as is illustrated in FIG. 8*b*. The at least one start of delivery sensor 101 (shown e.g. in FIG. 7*b*) is hereby activated by being pressed by the at least one protrusion 59 of the release member 54, as described above.

Figure 8C:
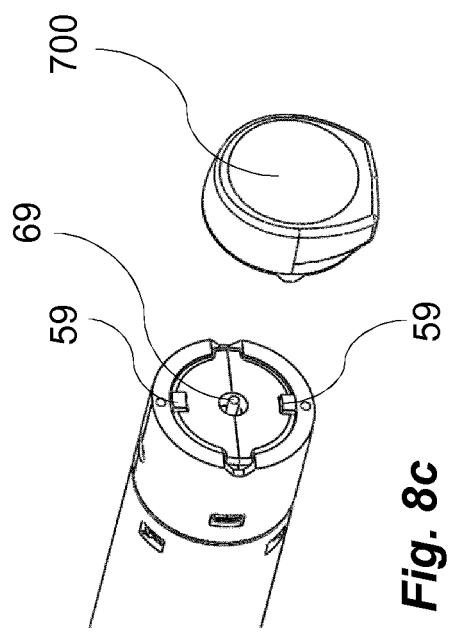
Figure 8D:
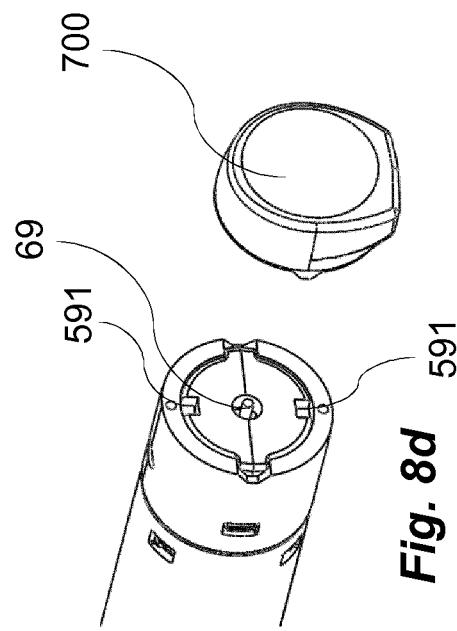

When the medicament has been delivered, the end of dose signaling member 66, and the guide rod member 65 and its protrusion 69, are forced distally, whereby the signaling member protrusion 69 extends through the hole/opening 691 and rises above the distal surface of the medicament delivery device 1, as shown in FIG. 8*c*. The end of delivery sensor 102 (shown e.g. in FIG. 7*b*) is hereby activated as described above.

When the needle guard 10 is moved proximally, e.g. by a user reducing the proximal force on the medicament delivery device 1, the release member 54 can, according to some embodiments described above, also be moved in the proximal direction. Hereby, also the at least one protrusion 59 of the release member 54 is moved proximally back into the medicament delivery device 1. Thus, the at least one release member protrusion 59 is withdrawn from above the distal surface/end of the medicament delivery device. The at least one protrusion 59 is then proximally moved away from the at least one start of delivery sensor 101, which is then deactivated. As state above, it is hereby possible to monitor if the needle guard has been moved proximally.

In FIGS. 2-7, such as e.g. in FIG. 7*b*, the electrical information device 100, 700 is for visibility reasons often exemplified as having one start of delivery sensor 101 configured/positioned to be activated/pressed by one release member protrusion 59. However, according to other embodiments of the present invention, more than one start of delivery sensor 101 may be included in the electrical information device 100, 700, e.g. two start of delivery sensors 101, each one being arranged to be activated/pressed by one of two release member protrusions 59. Usage of one start of delivery sensor 101 has an advantage in that few components are included in the electrical information device 100, 700, which lowers the complexity and the production costs for the device 100, 700. Usage of more than one start of delivery sensor 101 increases robustness of the electrical information device 100, 700.

The present invention is not limited to the above described embodiments. Instead, the present invention relates to, and encompasses all different embodiments being included within the scope of the independent claims.

The invention claimed is:

1. An electrical information device configured to communicate information related to a medicament delivery performed by a medicament delivery device; comprising:
at least one start of delivery sensor configured to detect a distal axial movement of a release member of said medicament delivery device, said release member being configured to be distally moved when an activator member of said medicament delivery device is forced distally by said medicament delivery device being pressed against a dose delivery site, wherein said at least one start of delivery sensor is configured to be directly contacted by at least one protrusion extending distally from a distal end of said release member when said release member performs said distal movement to thereby activate said at least one start of delivery sensor;

at least one information communication unit configured to communicate said information;

at least one activation unit configured to activate said at least one information communication unit based on said detected distal axial movement of said release member; and at least one end of delivery sensor spaced apart from the at least one start of delivery sensor, said at least one end of delivery sensor configured to detect a predetermined proximal axial movement of a plunger rod of said medicament delivery device, said predetermined proximal axial movement having a length $L_{pre}$ corresponding to a completed delivery of said medicament.

2. The electrical information device as claimed in claim 1, wherein an end of dose signaling member is configured to lose its support from said plunger rod when said plunger rod of said medicament delivery device has moved said length $L_{pre}$ proximally, whereby said end of dose signaling member is configured to be released from an initial fixed position and to perform an axial distal movement being detectable by said end of delivery sensor.

3. The electrical information device as claimed in claim 1, wherein said end of delivery sensor comprises:
at least one mechanical switch configured to be compressed by a distal movement of said end of dose signaling member.

4. The electrical information device as claimed in claim 1, wherein said end of delivery sensor comprises:
at least one mechanical switch configured to be compressed by a distal movement of at least one guide rod member being arranged within said end of dose signaling member.

5. The electrical information device as claimed in claim 1, wherein said end of delivery sensor comprises:
at least one electrical contact configured to be short-circuited by a distal movement of said end of dose signaling member.

6. The electrical information device as claimed in claim 1, wherein said end of delivery sensor comprises:
at least one electrical contact configured to be short-circuited by a distal movement of at least one guide rod member being arranged within said end of dose signaling member.

7. The electrical information device as claimed in claim 1, wherein said at least one start of delivery sensor includes one or more in the group of:
at least one mechanical switch configured to be compressed by said distal movement of said release member; and
at least one electrical contact configured to be short-circuited by said distal movement of said release member.

8. The electrical information device as claimed in claim 1, wherein said at least one start of delivery sensor is configured be deactivated by a proximal movement of said release member, said proximal movement of said release member being initiated by a proximal movement of said activator member.

9. The electrical information device as claimed in claim 1, wherein said at least one information communication unit includes at least one information indication arrangement.

10. The electrical information device as claimed in claim 9, wherein said information includes one or more in the group of:
at least one visual indication which indicates that said medicament delivery is in progress;

at least one audible indication which indicates that said medicament delivery is in progress;

at least one tactile indication which indicates that said medicament delivery is in progress;

at least one visual indication which indicates that said medicament delivery has ended;

at least one audible indication which indicates that said medicament delivery has ended;

at least one tactile indication which indicates that said medicament delivery has ended;

at least one visual indication which indicates that a predetermined time period has lapsed after said medicament delivery ended;

at least one audible indication which indicates that a predetermined time period has lapsed after said medicament delivery ended;

at least one tactile indication which indicates that a predetermined time period has lapsed after said medicament delivery ended; and an audible instruction which explains how said medicament delivery device should be handled.

11. The electrical information device as claimed in claim 9, wherein said at least one information indication arrangement includes one or more in the group of:

at least one light source configured to emit light as an indication;

at least one loudspeaker configured to emit an audible indication; and at least one tactile indication generating member.

12. The electrical information device as claimed in claim 3, wherein said at least one information communication unit includes at least one transmission unit configured to provide a wireless transmission of said information to at least one external receiving device.

13. The electrical information device as claimed in claim 12, wherein said information is based on preconfigured data and/or measured data related to said medicament delivery, said data comprising an identification number for said medicament delivery device.

14. The electrical information device as claimed in claim 12, wherein said information is based on preconfigured data and/or measured data related to said medicament delivery, said data comprising an identification number for a medicament being delivered by said medicament delivery device.

15. The electrical information device as claimed in claim 12, wherein said information is based on preconfigured data and/or measured data related to said medicament delivery, said data comprising an identification number for a patient using the medicament delivery device.

16. The electrical information device as claimed in claim 12, wherein said information is based on preconfigured data and/or measured data related to said medicament delivery, said data comprising:

an elapsed time since a delivery of a medicament occurred; and at least one indication of that said medicament delivery is in progress.

17. The electrical information device as claimed in claim 12, wherein said information is based on preconfigured data and/or measured data related to said medicament delivery, said data comprising:

at least one indication of that said medicament delivery has ended; and at least one indication of that a predetermined time period has lapsed after said medicament delivery ended.

18. The electrical information device as claimed in claim 3, wherein said electrical information device is included within a housing of said medicament delivery device.

19. The electrical information device as claimed in claim 3, wherein said electrical information device is included in an external unit, said external unit being releasably attachable to said medicament delivery device.

20. A medicament delivery device, comprising an electrical information device according to claim 1; and one or more of:

at least one release member including least one protrusion on its distal end, said at least one protrusion being configured to activate said at least one start of delivery sensor of said electrical information device if said at least one release member moves distally;

at least one guide rod member arranged within at least one end of dose signaling member, said at least one guide rod member including at least one protrusion on its distal end, said at least one protrusion being configured to activate at least one end of delivery sensor of said electrical information device if at least one guide rod member moves distally;

at least one end of dose signaling member including at least one protrusion on its distal end, said at least one protrusion being configured to activate at least one end of delivery sensor of said electrical information device if said end of dose signaling member moves distally; and at least one release member returning spring configured to move said release member proximally if said activator member moves proximally.

* * * * *